United States Patent [19]

Witherow

[11] 4,217,903

[45] Aug. 19, 1980

[54] DRAINAGE DEVICES

[76] Inventor: Ross O. Witherow, 17 De Beauvoir Sq., Islington, London N.1., England

[21] Appl. No.: 965,204

[22] Filed: Nov. 30, 1978

[30] Foreign Application Priority Data

Dec. 29, 1977 [GB] United Kingdom .............. 54185/77

[51] Int. Cl.³ ............................................. A61M 25/00
[52] U.S. Cl. ................................ 128/349 B; 128/243
[58] Field of Search ........... 128/349 R, 349 B, 350 R, 128/243

[56] References Cited

U.S. PATENT DOCUMENTS

| 2,919,697 | 1/1960 | Kim ................................... 128/349 B |
| 3,438,375 | 4/1969 | Ericson ............................. 128/349 B |

Primary Examiner—Dalton L. Truluck
Attorney, Agent, or Firm—Wheeler, Morsell, House & Fuller

[57] ABSTRACT

A drainage device, in particular a catheter, provided with an inflatable balloon adjacent one end which is designed to be inserted into a vessel which is to be drained. This insertion end comprises two branches which are interconnected at their free ends by the inflatable balloon and which are arranged, in the uninflated state of the balloon, to extend substantially parallel to the longitudinal axis of the device and to constitute substantially no increase in the width or diameter of the device. In the inflated state of the balloon, at least one of the said branches diverges from the longitudinal axis of the device to permit access to a drainage tube extending through the device.

4 Claims, 11 Drawing Figures

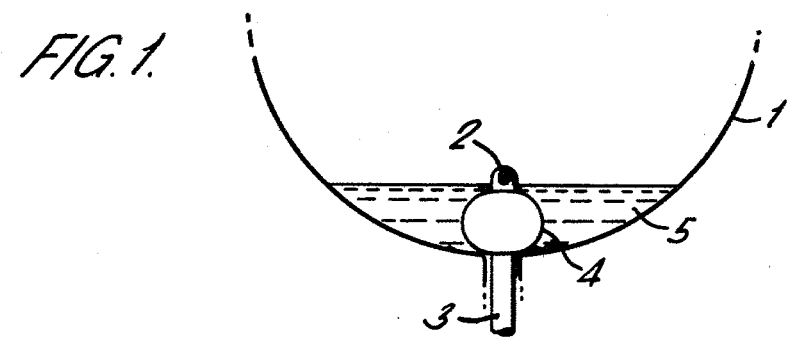
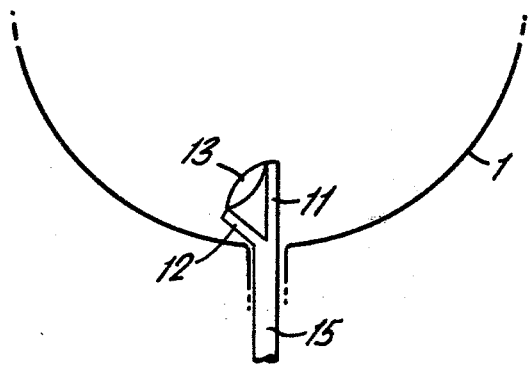
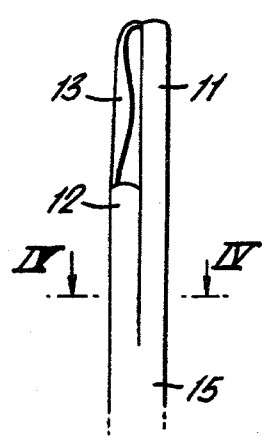
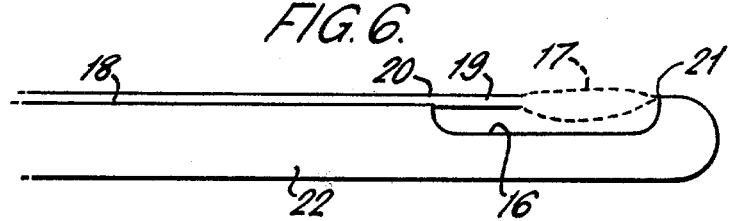

DRAINAGE DEVICES

BACKGROUND OF THE INVENTION

This invention relates to devices for draining vessels and is particularly concerned with catheters for draining organs and body cavities such as, for example, urinary bladder catheters.

Known cathers have a so-called balloon adjacent the insertion end which, once the catheter has been inserted into the bladder, is inflated to hold the catheter in position. The balloon surrounds the drainage tube in the known catheters and thus causes an increase in the diameter of the catheter in the balloon region even when the balloon is not inflated. Any increase in the diameter of a catheter is disadvantgeous since it impedes the insertion of the catheter through the urethra into the bladder.

A further disadvantage of the known catheters is that, once inserted into the bladder and with the balloon inflated, the inlet to the drainage tube at the end of the catheter is spaced from the bladder wall by the length of the balloon so that a quantity of urine can collect and remain in the bladder as shown in FIG. 1 of the drawings. This residual urine can cause infection of the bladder and encrustation of products on the surface of the catheter.

SUMMARY OF THE INVENTION

The object of the present invention is to provide a catheter which will overcome the above-mentioned disadvantages inherent in the known catheters.

A further object of the invention is to provide a device for draining a vessel which permits the vessel to be substantially entirely drained of liquids.

According to the invention, there is provided a catheter provided with an inflatable balloon adjacent its insertion end, wherein the said insertion end comprises at least two branches interconnected at their free ends by the inflatable balloon, said branches being arranged, in the uninflated state of the balloon, to extend substantially parallel to the longitudinal axis of the catheter and to constitute substantially no increase in the width or diameter of the catheter and, in the inflated state of the balloon, at least one of said branches diverging from the longitudinal axis of the catheter to permit access to the drainage tube of said catheter.

Preferably, two branches are provided, one of said branches terminating at the insertion end of the catheter and the other branch terminating short of said end.

BRIEF DESCRIPTION OF THE DRAWINGS

The invention will now be further described, by way of example, with reference to the drawings, in which:

FIG. 1 illustrates diagrammatically a known catheter located in a bladder;

FIG. 2 is a view corresponding to FIG. 1 but showing one embodiment of a catheter according to the invention;

FIG. 3 is a view of the insertion end of the catheter shown in FIG. 2 but showing the balloon in the uninflated condition;

FIG. 4 is a section taken on the line IV—IV in FIG. 3;

FIG. 5 is a section corresponding to FIG. 4 but showing a modification;

FIG. 6 is a side elevation of the insertion end of a second embodiment of a catheter according to the invention showing the balloon in the uninflated state;

In the drawings, like parts are denoted by like reference numerals.

DESCRIPTION OF PREFERRED EMBODIMENTS

Figure 7:
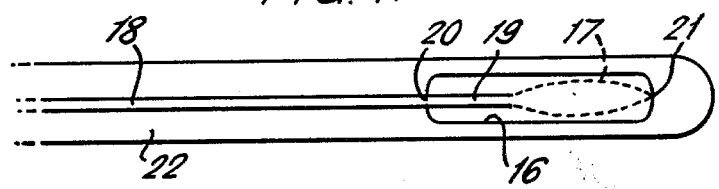
FIG. 7 is a plan view of the catheter shown in FIG. 6.

Referring to the drawings, the catheter shown in FIG. 1 is provided with an opening 2 adjacent the insertion end by means of which urine in the bladder 1 may pass down the drainage tube 3. The opening 2 is spaced from the wall of the bladder 1 by an inflated balloon 4, which secures the catheter in position, and thus a pool of residual urine 5 collects in the bladder and cannot be drained. This residual urine can cause infection of the bladder and encrustation of products on the surface of the catheter. Therefore with the known catheter frequent replacement is necessary in order to reduce the risk of infection. Such risk is, however, always present.

The catheter according to the invention enables the bladder to be drained substantially completely as can be seen from FIG. 2 of the drawings. The insertion end of the catheter is divided into two branches 11 and 12, the branch 11 extending to the end of the catheter while the branch 12 terminates short of said end. The end of branch 12 is connected to the end of branch 11 by a balloon 13 and, when not inflated, the outer surface of the balloon is substantially contiguous with the outer surface of the branch 12 and with the rest of the catheter as shown in FIG. 3 so that the balloon represents no increase in the width or diameter of the catheter thereby rendering insertion into the bladder through the urethra far easier than with the known catheters in which the balloon region represents a thickening or enlargement of the width or diameter of the catheter.

Once inserted into the bladder 1, the balloon can be inflated in known manner through the water tube 14 (FIG. 4) when it assumes the position shown in FIG. 2 of the drawings. It will be observed that, with the balloon inflated, the branches 11 and 12 diverge from one another and thus hold the catheter in position. The branch 12 accommodates the water tube 14 as shown in FIG. 4 while the branch 11 has an open side facing the branch 12 and balloon 13 by means of which urine can pass into the drainage tube 15. Since the open side of branch 11 is located adjacent the bladder wall, substantially all of the urine can be drained from the bladder so that a pool of residual urine is not formed in this case.

Instead of the water tube 14 being located within the branch 12 as shown in FIG. 4, the branch 12 may also be provided with an open side facing the branch 11 as shown in FIG. 5 and the water tube 14 can then be provided on the outside of this branch.

Figure 8:
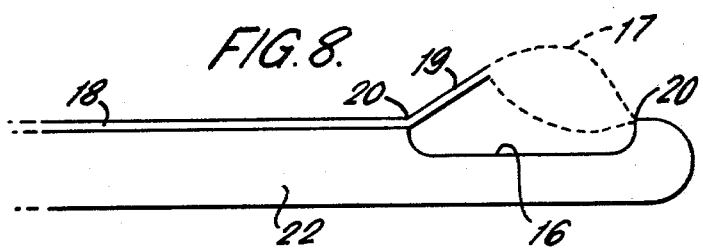
FIG. 8 is a side elevation of the catheter shown in FIG. 6 but showing the balloon in the inflated state.

The embodiment shown in FIGS. 6 to 8 of the drawings differs from the embodiment shown in FIGS. 2 to 4 in that the catheter is provided at its insertion end with a cut-out region 16 which is bridged by an inflatable balloon 17 and a balloon filling channel 18. As shown in FIG. 6, when the balloon 17 is not inflated it is accommodated substantially completely within the region 16 and thus does not constitute any increase in the diameter of the catheter. At least the bridge portion 19 of the channel 18 is made of flexible material so that the said bridge portion can pivot about the point 20 when the balloon is inflated as shown in FIG. 8. One end of the balloon 17 is connected to the projecting end of the bridge portion 19 of the channel 18 and the interior of the balloon is in communication with the interior of the channel 18. The other end of the balloon 18 is attached at point 21 to the main drainage tube 22 of the catheter in which the cut-out region 16 is provided. The end of the region 16 remote from the balloon connection point 21 can be positioned adjacent the bladder wall so that substantially all of the urine can be drained from the bladder and the formation of a pool of residual urine is prevented.

Figure 9:
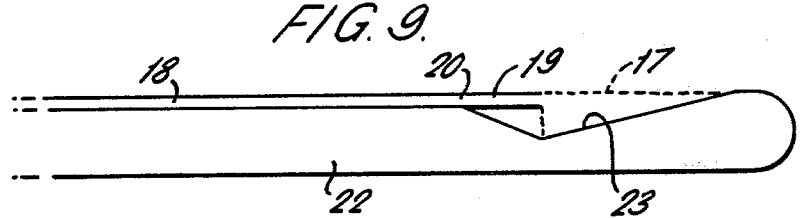
FIG. 9 is a side elevation of the insertion end of a third embodiment of a catheter according to the invention showing the balloon in the uninflated state.
Figure 10:
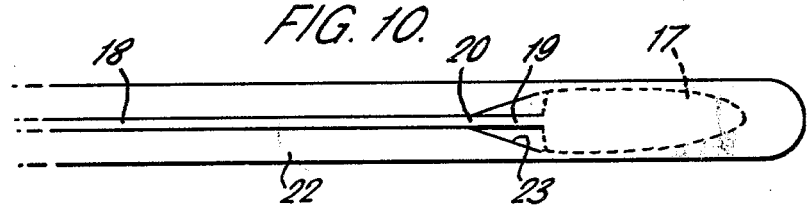
FIG. 10 is a plan view of the catheter shown in FIG. 9.
Figure 11:
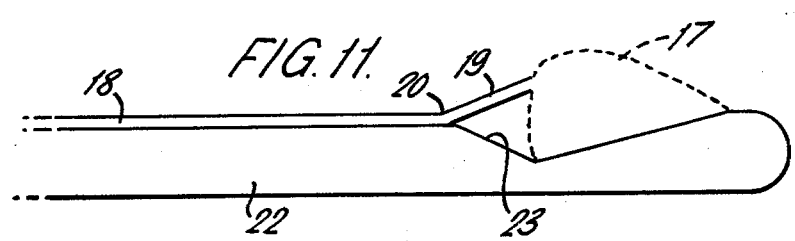
FIG. 11 is a side elevation of the catheter shown in FIG. 9 but showing the balloon in the inflated state.

The embodiment shown in FIGS. 9 to 11 of the drawings is similar to the embodiment shown in FIGS. 6 to 8 except that in this case the drainage tube 22 is provided with a V-shaped cut-out region 23 and the surface of the balloon 17 facing the tube 22 is bonded to said tube. This arrangement produces a more streamlined catheter. This catheter functions in the same manner as that described with reference to FIGS. 6 to 8 of the drawings.

Manufacture of catheters according to the invention is simpler than with the known self-retaining balloon catheters because the additional process of surrounding the drainage tube by an inflatable balloon is avoided. Moreover, the width or diameter of a catheter according to the invention is substantially uniform since the added width at the balloon region in known catheters is also avoided. Furthermore, since the catheters according to the invention prevent the retention of residual urine in the bladder, the likelihood of infection and encrustation of products onto the catheter surface is greatly reduced so that the frequency of catheter changing can also be reduced.

The invention is not restricted to catheters but is equally applicable to other devices for draining vessels. Thus, the present invention also provides a device for draining vessels comprising a drainage tube terminating at one end in at least two branches, the free ends of at least two said branches being interconnected by an inflatable balloon. Such a device may have one or more of the preferred features of the catheters described above.

Other embodiments and modifications are possible without departing from the scope of the invention as defined by the appended claims.

I claim:

1. A catheter adapted for insertion into a body cavity, said catheter having an insertion end and a drainage tube and being further provided with an inflatable balloon adjacent said insertion end and a balloon filling channel; said insertion end comprising two branches having free ends which are inter-connected by the inflatable balloon, one of said branches terminating at the end of said insertion end of the catheter and the other said branch terminating short of said end; said branches being arranged, in the uninflated state of the balloon, to extend substantially parallel to the longitudinal axis of the catheter and to constitute substantially no increase in the width or diameter of the catheter; said one branch comprising an extension of the drainage tube of the catheter and the balloon filling channel being located in one of said branches and being in communication with the interior of the balloon, said balloon being arranged to be inflated by passing fluid through said filling channel and, in the inflated state of the balloon, said other branch diverging from the longitudinal axis of the catheter, an opening leading to the drainage tube being located between said branches and one end of said opening being spaced from the balloon to permit substantially complete emptying of fluids from a body cavity into which the catheter has been inserted.

2. A catheter as claimed in claim 1, in which said one branch is provided with a cut-out region adjacent said insertion end and in which said cut-out region is bridged by the said other branch and the balloon.

3. A catheter as claimed in claim 2, in which the said other branch comprises part of said balloon filling channel the interior of which is in communication with the interior of the balloon.

4. A catheter as claimed in claim 2, in which a portion of the outer surface of the balloon is secured to the said one branch.

* * * * *